US006375996B1

(12) United States Patent
Suter et al.

(10) Patent No.: US 6,375,996 B1
(45) Date of Patent: Apr. 23, 2002

(54) METHOD AND SYSTEM FOR PROCESSING PULP AND JUICE IN A JUICE FINISHER

(75) Inventors: Michael L. Suter, Spring Hill; Gregory Schrader; Salvador Garcia, both of Lakeland, all of FL (US); Jose Flores, San Pedro Garza Garcia (MX)

(73) Assignee: FMC Technologies, Inc., Chicago, IL (US)

( * ) Notice: Subject to any disclaimer, the term of this patent is extended or adjusted under 35 U.S.C. 154(b) by 41 days.

(21) Appl. No.: 09/678,606

(22) Filed: Oct. 4, 2000

(51) Int. Cl.$^7$ .......................... A23N 1/00; G01N 33/00
(52) U.S. Cl. ........................ 426/231; 99/495; 99/510; 426/489
(58) Field of Search ........................ 426/231, 489, 426/519, 521; 99/495, 510, 513; 73/73

(56) References Cited

U.S. PATENT DOCUMENTS

| | | | |
|---|---|---|---|
| 1,822,604 A | 9/1931 | Simons et al. .................. 73/73 |
| 2,799,823 A | 7/1957 | Shaw et al. ................... 324/0.5 |
| 2,999,381 A | 9/1961 | Chope et al. ................... 73/73 |
| 3,621,379 A | 11/1971 | Watson et al. ............... 324/0.5 |
| 3,966,973 A | 6/1976 | Henry et al. ................. 426/231 |
| 4,542,343 A | 9/1985 | Brown ....................... 324/307 |
| 4,665,816 A | 5/1987 | Waters et al. ................. 100/38 |
| 4,701,705 A | 10/1987 | Rollwitz ..................... 324/306 |
| 4,868,500 A | 9/1989 | Baldwin et al. ............. 324/307 |
| 5,162,733 A | 11/1992 | Baldwin ..................... 324/307 |
| 5,207,154 A | 5/1993 | Bonnet ........................ 100/37 |
| 5,388,507 A | 2/1995 | Bonnet ........................ 100/37 |
| 5,539,309 A | 7/1996 | Van Wyk et al. ........... 324/307 |
| 5,770,251 A | * 6/1998 | Finucane et al. ........... 426/231 |
| 5,992,311 A | 11/1999 | Suter et al. .................... 100/37 |

OTHER PUBLICATIONS

Cho et al., "Nondestructive Sugar Content Measurements of Intact Fruit Using Spin–Spin Relaxation Time (T2) Measurements By Pulsed $^1$H Magnetic Resonance," American Society of Agricultural Engineers, vol. 36(4), Jul.–Aug. 1993, pp. 1217–1221.

Stroshine et al., "Magnetic Resonance Sensing of Fruit Firmness and Ripeness," American Society of Agricultural Engineers, Paper No. 91–6565, pp. 1–13.

Stroshine, "Nondestructive Sensing of Fruit and Vegetable Ripeness and Food Quality," Research Paper, Research Activities 1993, p. 26.

Ray et al., "Quality Sorting of Sweet Cherries Using Magnetic Resonance," American Society of Agricultural Engineers, Paper No. 93–6071.

Stroshine et al., "An ASAE Meeting Presentation Non–Destructive Ripeness Sensing of Intact Avacado, Nectarine and Orange Using Proton Magnetic Resonance," American Society of Agricultural Engineers, Paper No. 93–6535.

Schrader et al., "Magnetic Resonance Imaging Applications in the Food Industry," Food Technology, Dec. 1992, pp. 77–83.

Chen et al., "NMR For Internal Quality Evaluation of Fruits and Vegetables," American Society of Agricultural Engineers, vol. 32(5), Sep.–Oct. 1989, pp. 1747–1753.

Belton et al., "Nuclear Magnetic Resonance Spectroscopy in Food Research," Spectroscopy, vol. 4, No. 9, pp. 22–32.

* cited by examiner

Primary Examiner—George C. Yeung
(74) Attorney, Agent, or Firm—Allen, Dyer, Doppelt, Milbrath & Gilchrist, P.A.

(57) ABSTRACT

The method and system of the present invention measures pulp dryness using nuclear magnetic resonance (NMR). It also controls the discharge of pulp and juice from a juice finisher. The discharge from the juice finisher is measured using the sensor. Based on the results of the NMR measurement, one of at least the juice injection into the juice finisher, the speed of the juice finisher, or the discharge pressure from the juice finisher is regulated.

21 Claims, 7 Drawing Sheets

METHOD AND SYSTEM FOR PROCESSING PULP AND JUICE IN A JUICE FINISHER

FIELD OF THE INVENTION

This invention relates to the field of fruit and vegetable processing, and more particularly, this invention relates to controlling the discharge of pulp and juice in a juice finisher.

BACKGROUND OF THE INVENTION

The juice extraction process is well known to those skilled in the art, such as described in U.S. Pat. No. 5,992,311, assigned to the present assignee, the disclosure which is hereby incorporated by reference in its entirety. A fruit, vegetable and the like is fed to a juice extractor, which acts as the primary extractor, and produces a pure liquid (juice) and a fibrous material (pulp) from fruit, vegetables and the like. After extraction, this mixture of juice and pulp is fed as a stream into a juice finisher, which is designed to separate the juice from the pulp.

The typical juice finisher used in a citrus processing facility includes either a screw type finisher and/or a paddle finisher. Both types of finishers rely on the juice to be extruded through a screen material, which regulates the size of the pulp that is maintained within the juice stream. Any pulp that is too large to be extruded through this screen is compressed by centrifugal and mechanical force, which is created by limiting the flow of pulp discharge either by a back pressure regulator and/or a weighted gate. With both types of finishers, the feed rate and the pulp-to-juice ratio of the feed material has a dramatic affect on the level of dryness at a given condition. Feed forward control is often used and based on historical data. It is usually used to control a screw type finisher. This type of control requires close monitoring as fruit conditions change.

The dryness of pulp can be determined within prior art systems by using the free liquid that is removed without the application of pressure, in a method known as the quick fiber method. This is the defacto standard for the calibration of finishers to maximize juice and juice by-products for yield and quality. Typically, a sample of pulp is brought to a laboratory where tests are conducted on the sample. For example, 200 grams of pulp sample are mixed with about 200 milliliters of water and stirred for a minute. This mixture sits for three minutes and is then stirred for another minute. The mixture is placed into a shaker with a 40 mesh screen for about three minutes and the liquid retrieved from the sample. The liquid is measured in a graduated cylinder where the amount of liquid measured (in milliliters) is called quick fiber. The total time is about 8–10 minutes, with even more time for preparation. This process is an established procedure that is time consuming. Additionally, the procedure has low accuracy, i.e., not repeatable, and high labor intensity, making this quick fiber method inefficient and costly.

Another drawback with prior art methods are the feed forward control. As noted before, the feed forward control is based on historical data, which is used to control a screw type finisher. This control requires close monitoring as fruit conditions change. Although feed forward control is better than simple manual control, it does not work on a paddle finisher and has no self-correction capability, thus eliminating the need for supervision.

U.S. Pat. No. 4,665,816 to Waters et al. discloses an apparatus that automatically controls a juice finishing machine. The temperature of juice solids in a pad area and temperature of initial juice entering the machine are separately monitored. A differential output signal is established and used for controlling machine operation. This is more complex than desired.

SUMMARY OF THE INVENTION

The present invention provides a system and method that advantageously controls the discharge of pulp and juice from a juice finisher without requiring the use of the more conventional quick fiber method. In accordance with one aspect of the present invention, a sample of pulp is obtained from juice, and pulp dryness measured using nuclear magnetic resonance (NMR). A juice and pulp processing system can be adjusted in response to the measured pulp dryness. In yet another aspect of the present invention, the discharge from the juice finisher that processes pulp and juice is measured using a nuclear magnetic resonance sensor. Based on the results of the NMR measurement, one of at least the juice injection into the juice finisher, the speed of the juice finisher, or the discharge pressure from the juice finisher is regulated.

In yet another aspect of the present invention, the NMR sensor measures the pulp dryness of pulp discharged from the juice finisher and compares the pulp dryness with a predetermined setpoint. If the pulp dryness differs from the predetermined setpoint, the speed of the juice finisher is changed. If the measured dryness is less than the predetermined setpoint, the speed of the finisher is decreased, and if the dryness is greater than the predetermined setpoint, the speed of the finisher is increased. The juice finisher could include a paddle type finisher.

In yet another aspect of the present invention, the NMR sensor measures the pulp dryness of pulp that is discharged from the juice finisher and compares the pulp dryness with a predetermined setpoint. If the pulp dryness differs from the predetermined setpoint, the pressure is changed within the juice finisher. In one aspect of the present invention, if the measured dryness is less than the predetermined setpoint, then the pressure is decreased. If the measured dryness is greater than the predetermined setpoint, the pressure is increased.

In yet another aspect of the present invention, the NMR sensor measures the ratio of pulp to juice in the juice finisher and compares the measured results with a predetermined setpoint. If the measured results differ from the setpoint, the juice injection into the finished pulp is changed for maintaining a desired pulp concentration level. If the measured results are less than the setpoint, the juice injection into the finished pulp is decreased. If the measured results are above the setpoint, the juice injection into the finished pulp is increased. The juice finisher could include a juice concentrator.

A fruit processing system also controls the discharge of pulp and juice and includes a juice finisher that receives juice and pulp from a juice extractor and separates the juice and pulp into a discharge substantially made of pulp and a discharge substantially made of juice. A nuclear magnetic resonance (NMR) sensor measures the dryness of the pulp discharged from the juice finisher. A controller compares the measured result with a predetermined setpoint and outputs a finisher control signal to the juice finisher for changing operation of the finisher.

In yet another aspect of the present invention, a variable speed drive is operatively connected to the juice finisher and responsive to the finisher control signal for decreasing the speed of the juice finisher if the measured dryness is less than a predetermined setpoint. The speed of the juice finisher is increased if the measured dryness is greater than the predetermined setpoint. A current-to-pressure transmitter can be connected to the juice finisher and responsive to a finisher control signal for decreasing pressure when the measured dryness is less than the predetermined setpoint and increasing pressure when the measured dryness is greater than the predetermined setpoint.

In yet another aspect of the present invention, the juice finisher is formed as a juice concentrator, i.e., pulp concentrator that separates juice and a juice and pulp mixture. The controller determines the ratio of pulp to juice in the juice and pulp mixture. A mixer receives the juice and pulp mixture. A portion of the juice is fed back from the juice finisher. A valve is operatively connected to the controller and operative for changing the flow of juice into the mixer.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The present invention is advantageous and uses nuclear magnetic resonance (NMR) to measure the discharge of a paddle and/or screw type finisher for pulp dryness, feeding back a signal to a control system that regulates the flow to the finisher, and/or the speed of the finisher, and/or discharge gate pressure to achieve a desired level of dryness or uniform ratio of pulp to juice. The invention is more advantageous than the prior art use of the quick fiber method, which was expensive, time consuming, and not repeatable. Additionally, the system and method of the present invention can be used in a pasteurization system and other similar systems, where a juice finisher and/or juice concentrator separates juice from a juice and pulp mixture, and then mixes juice in a mixer with the pulp mixture to provide a desired ratio.

Figure 1:
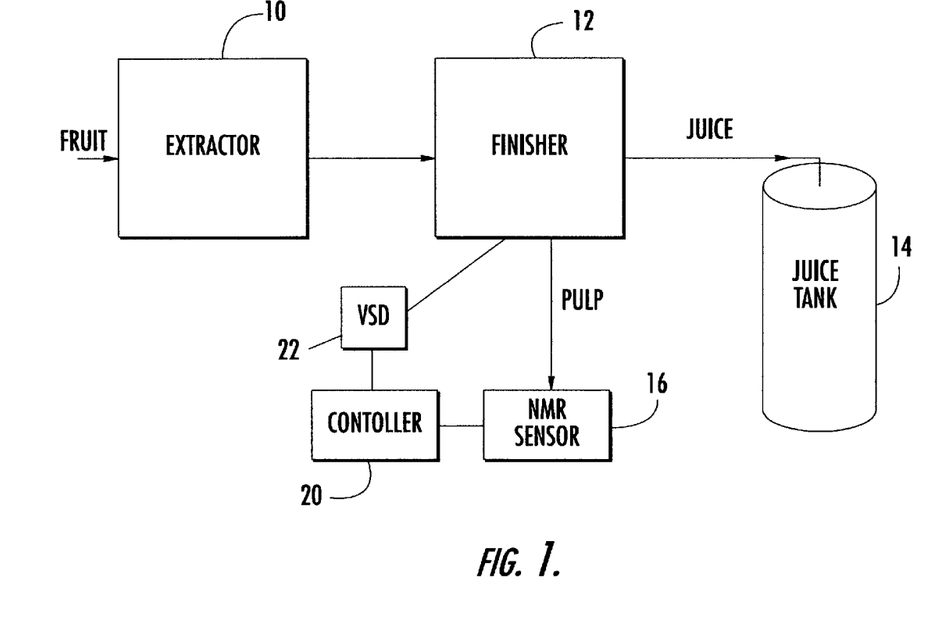
FIG. 1 is a block diagram of a juice extractor, juice finisher, showing the NMR sensor, controller, and variable speed drive connected to the juice finisher.
Figure 3:
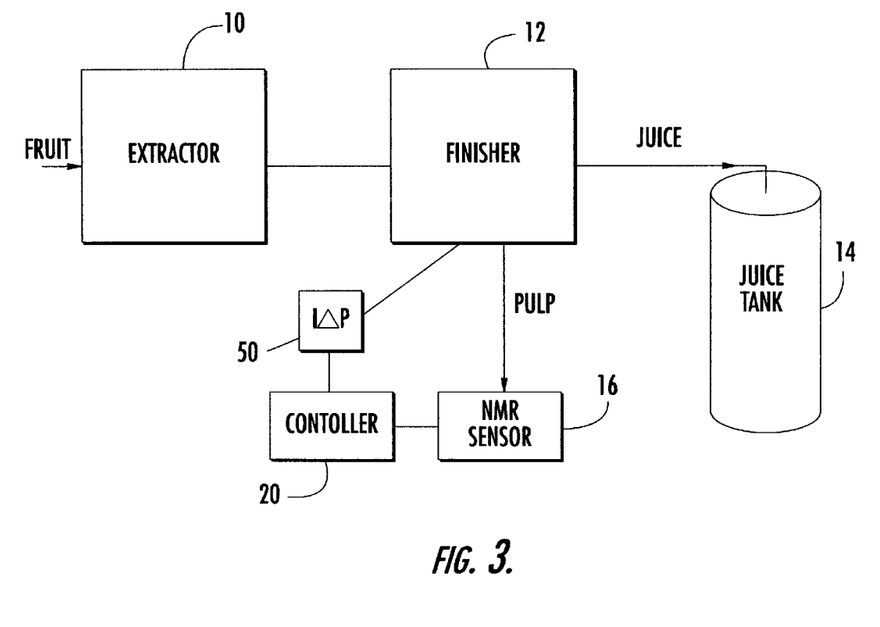
FIG. 3 is another block diagram of a juice extractor, juice finisher and NMR sensor with the current-to-pressure transmitter attached to the juice finisher.

As shown in FIGS. 1 and 3, basic block diagrams of the juice and pulp processing system are illustrated. Similar elements are given like reference numerals throughout the description. Fruit, such as an orange, or a vegetable, is fed into the juice extractor 10, where juice and pulp are extracted therefrom as a stream of liquid juice and pulp. A juice finisher 12 receives the juice and pulp and produces juice, as is well known to those skilled in the art, which is delivered to juice tank 14. The finisher 12 could be a paddle or screw type finisher. A screw type finisher typically includes a gate valve, which is often not included in a paddle type finisher. These type of finishers are well known to those skilled in the art.

An NMR sensor 16 receives pulp from the finisher and determines the dryness of the pulp. Typically, a sample of pulp is positioned in the sensor assembly of an NMR spectrometer and a NMR pulse sequence applied to measure pulp dryness as a function of the spin-spin relaxation time.

As is known to those skilled in the art, nuclear magnetic resonance (NMR) technology is a non-destructive testing tool. A hydrogen proton has a nuclear spin resulting in a microscopic magnetization vector. Before being placed in a magnetic field, there is no net magnetization because of random orientation of the vector. When placed in a magnetic field, the atoms align with the field at a displacement angle and are in an anti-parallel state pointing in one direction. Other atoms, often a greater quantity of atoms, are in a lower energy parallel state pointing in the opposite direction, resulting in a different magnetization vector. A high pulse at a nuclear magnetic resonance (NMR) frequency is generated to rotate the magnetization vector, such as a vector of 90°. This magnetic vector begins to precess in the x/y plane about the z-axis, and a coil, placed in the same plane, receives an electrical signal to measure the relaxation properties of the hydrogen protons as they return to their original position.

An example of the type of NMR apparatus that can be used with the present invention is a Discover 1000 NMR sensor, such as manufactured by Magnetic Instrumentation, Inc. of Indianapolis, Ind. One skilled in the art, however, recognizes that different types of NMR instruments can be used, including various types of continuous and pulsed NMR sensors.

The pulsed NMR is more versatile and powerful and is the predominant type of NMR used today for this type of application. The spin-spin relaxation time or $T_2$ is one of several parameters usually extracted from pulsed NMR spectra, which is used to study water. The NMR signal in the time domain, the free induction decay (FID), is a complex superposition of the relaxation behavior ($T_2^*$) from all nuclei. $T_2^*$ is the sum of pure $T_2$ plus the contribution from the inhomogeneity in the sample and magnet. For simplicity, however, $T_2^*$ is often reported as $T_2$. Different components or phases in the sample relax at different rates. By examining the shape of the FID, one can often determine the contents of different components or phases.

The NMR based sensing system, in one non-limiting example, is a low field spectrometer which consists of three assembly units: processing electronics, power and sensor. The processing electronics assembly consists of a processor with three unique cards (signal generator, receiver and analog-to-digital converter cards). The power assembly contains an RF power amplifier and a DC power supply. The sensor assembly uses a magnet assembly that permits a sample diameter of 1", and also includes a transmit/receive assembly, as well as a temperature sensor.

During operation, the processing electronics subsystem generates a low level signal under software control. that is fed to the power assembly. It is amplified and fed to the sensor assembly. Signals received from the sample in the sensor assembly are then amplified and fed to the receiver where they are demodulated and processed to determine the amount of juice left in the sample.

Figure 7:
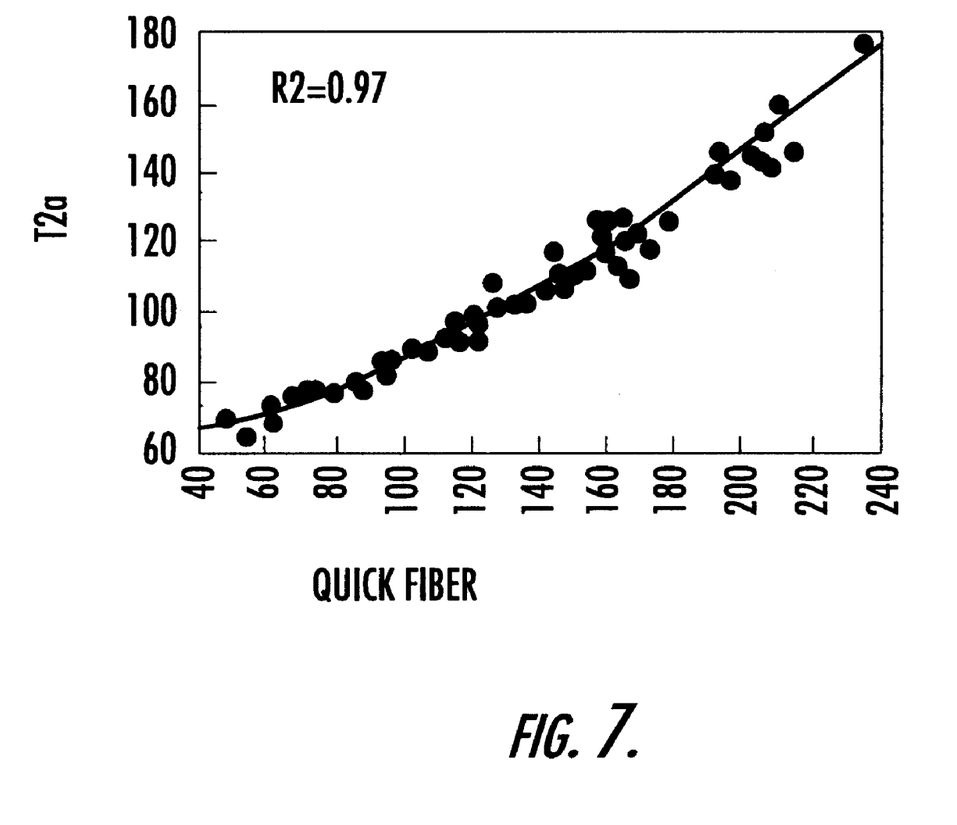
FIG. 7 is a graph showing a correlation between the measurement of $T_2$, using NMR and quick fiber.

In one analysis using the system and method of the present invention, the results and values obtained from the NMR spectrometer and system were compared to those obtained from the quick fiber method. Preliminary results obtained from these tests indicate that there was a high correlation between the measurement of $T_2$, using NMR, and quick fiber (FIG. 7). In over 90% of all samples, it was possible to predict the quick fiber measurement within ten quick fiber points. It is likely that any differences may be due to the inaccuracies in the quick fiber measurement and not to the $T_2$ measurement. $T_2$ measurement can be done very rapidly ($\approx$3 seconds), the results are highly repeatable, and it is not affected by sample preparation or other conditions of the sample.

FIG. 1 illustrates the method and system of the present invention where fruit, vegetable or the like is processed through the juice extractor 10 and juice finisher 12. Juice is fed as a stream from the juice finisher 12 into the juice tank 14, while pulp is discharged. A sample of pulp is analyzed by the NMR sensor 16 and the results fed into a controller 20, where the pulp dryness is compared with a predetermined setpoint. The controller 20 is operatively connected to the variable speed drive 22 of the juice finisher 12. If the pulp dryness differs from the predetermined setpoint, the speed of the juice finisher is changed.

Figure 2:
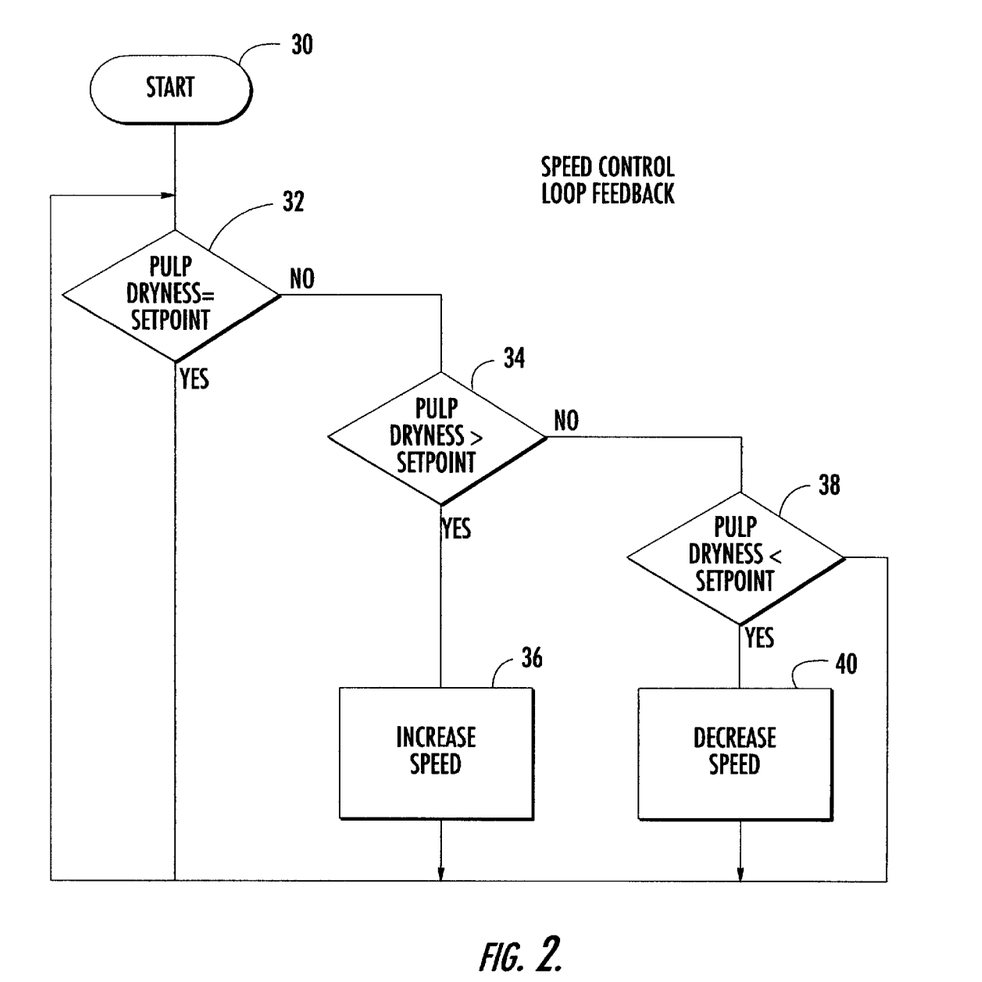
FIG. 2 is a flow chart illustrating a speed control loop feedback for the operation of the juice finisher shown in FIG. 1.

FIG. 2 illustrates a flow chart of the method that can be used with the juice finisher shown in FIG. 1. At the start (block 30), the pulp sample is retrieved and the pulp dryness determined and compared to the setpoint at block 32. If the pulp dryness is at setpoint, then the loop continues and no changes are made to the speed.

If the pulp dryness does not equal a setpoint and the pulp dryness is greater than the setpoint (block 34), then the speed is increased (block 36) in a speed control loop feedback, such as by the controller 20 issuing a speed control command to the variable speed drive 22. If the pulp dryness is less than the setpoint (block 38), then the speed is decreased (block 40).

FIG. 3 illustrates another block diagram similar to FIG. 1, but showing that the juice finisher 12 also includes a current-to-pressure transmitter (I$\Delta$P) 50 that allows pressure control over the juice and pulp contained within the juice finisher. The pulp is measured in the NMR sensor 16 as before, and the controller 20 compares the pulp dryness with a predetermined setpoint. If the pulp dryness differs from the predetermined setpoint, the pressure is changed within the juice finisher 12. If the measured dryness is less than the predetermined setpoint, the pressure is decreased. If the measured dryness is greater than the predetermined setpoint, pressure is increased.

Figure 4:
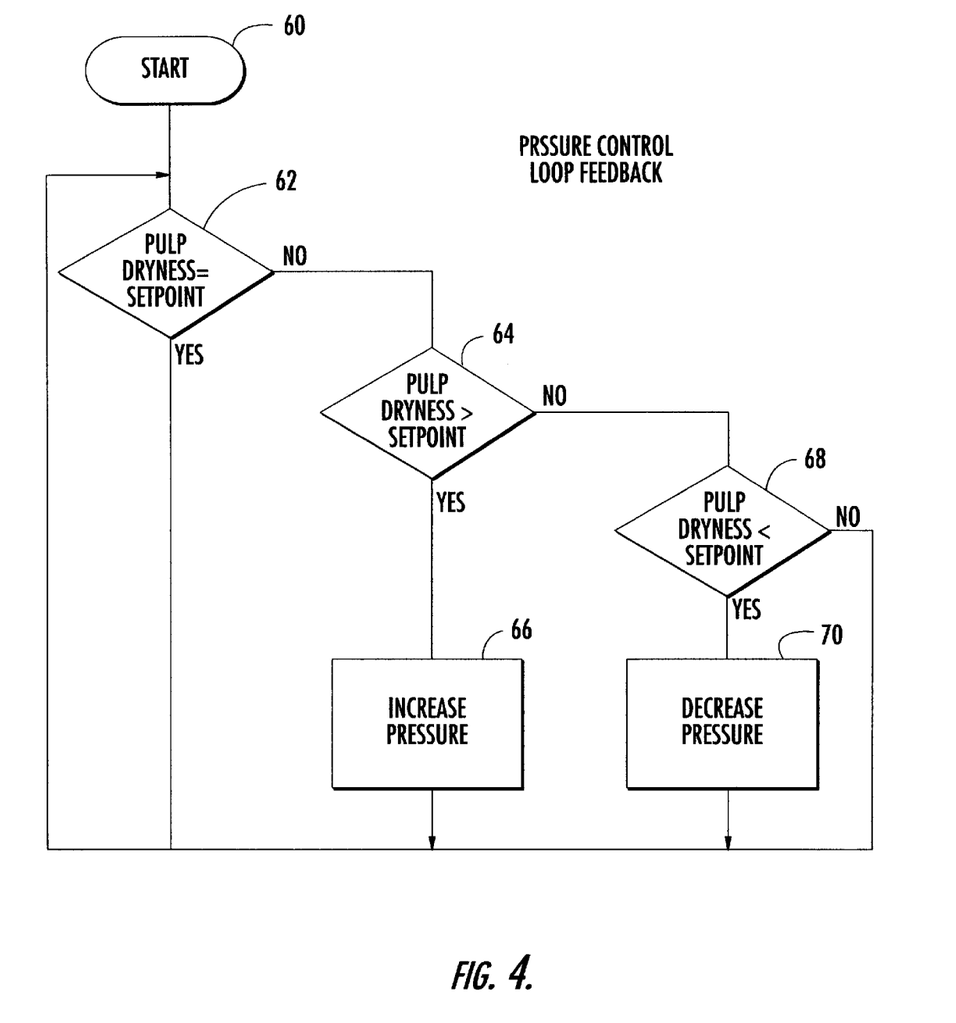
FIG. 4 is a flow chart illustrating the pressure control loop feedback used for the juice finisher shown in FIG. 3.

As shown in the flow chart of FIG. 4, illustrating the pressure control loop feedback, the process starts (block 60) and a determination is made whether the pulp dryness is at setpoint (block 62). If yes, then the loop continues as before. If the pulp dryness is not at setpoint, and is greater than the setpoint (block 64), the pressure is increased (block 66). If the pulp dryness is not greater than the setpoint, a determination is made if the pulp dryness is less than setpoint (block 68), and if not, the loop continues because it is substantially equal. If the pulp dryness is less than setpoint, the pressure is decreased (block 70) by controlling the pressure tap 50 via a pressure control signal issued by the controller 20.

Figure 6:
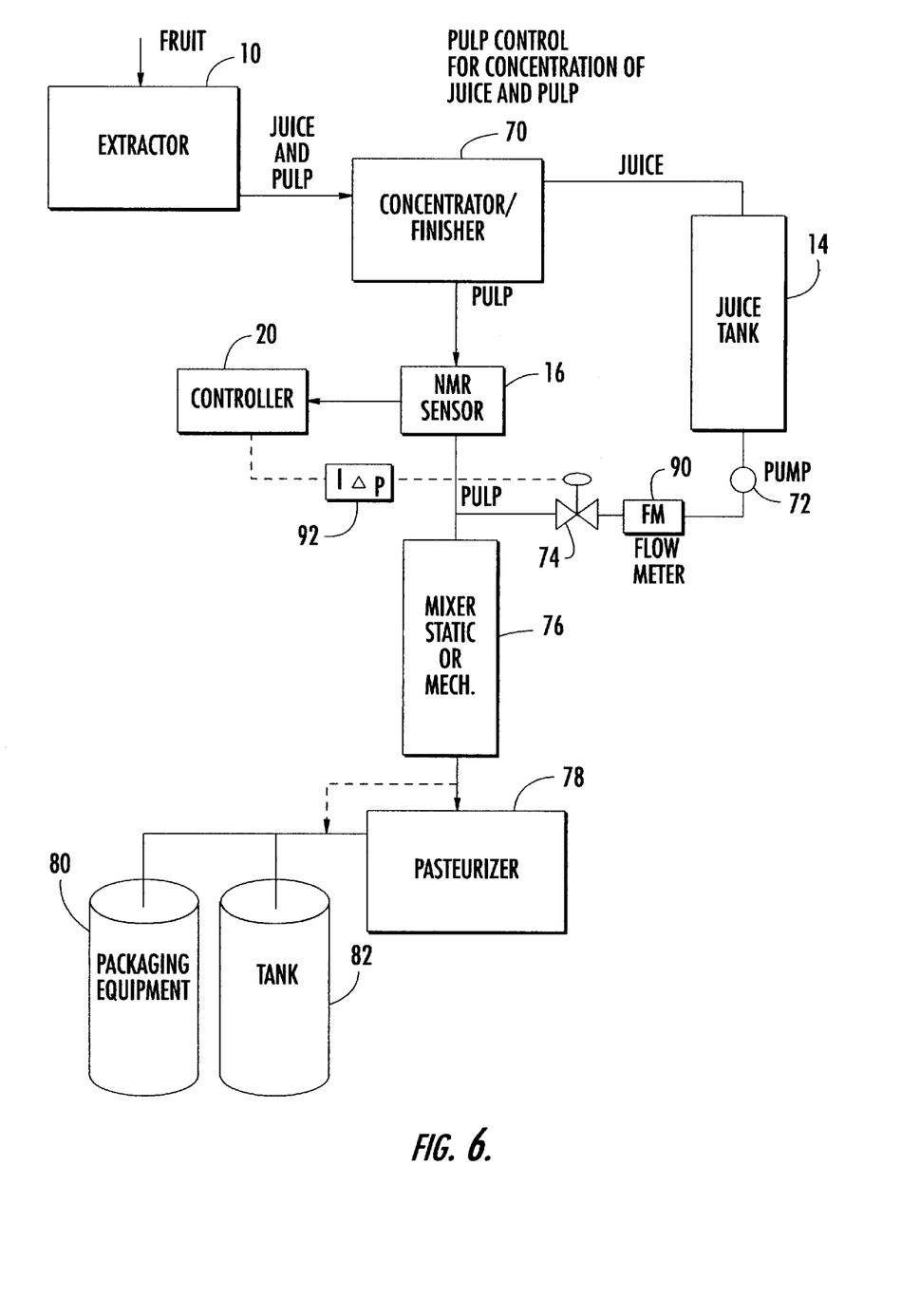
FIG. 6 is a block diagram of a juice finisher system that uses the method shown in FIG. 5.

FIG. 6 illustrates a block diagram of yet another aspect for a system and method of the present invention, where a juice finisher, in the form of a juice or pulp concentrator 70, receives the juice and pulp from the juice extractor 10, as known to those skilled in the art. The juice finisher outputs a juice stream into the juice tank 14 and a juice and pulp mixture (substantially pulp), where the ratio of the pulp juice, such as in grams/liter of pulp to juice, is determined. In this system, a juice tank pump 72 pumps juice from the juice tank through a valve 74 into a mixing tank 76, where the juice is mixed with the juice and pulp mixture from the finisher. The mixer could be a static or mechanical mixer. A static mixer mixes the juice with the pulp to provide a well mixed product to downstream equipment. The downstream equipment could include a pasteurizer 78 for additional processing and packaging equipment 80 and another juice tank 82, which could also be connected to a pasteurizer, if used. These types of components are well known to those skilled in the art. As illustrated, the NMR sensor receives the juice and pulp and measures the pulp concentration, as noted above. A flow meter 90 also is connected within the supply line between the valve 74 and pump 72 for the juice tank 14. The controller 20 is operatively connected to the NMR sensor 16, a current-to-pressure transmitter 92 and the control of the valve 74. The use of a flow meter on the juice stream feeding into the mixer will enhance control and allow more mass balanced prediction.

Figure 5:
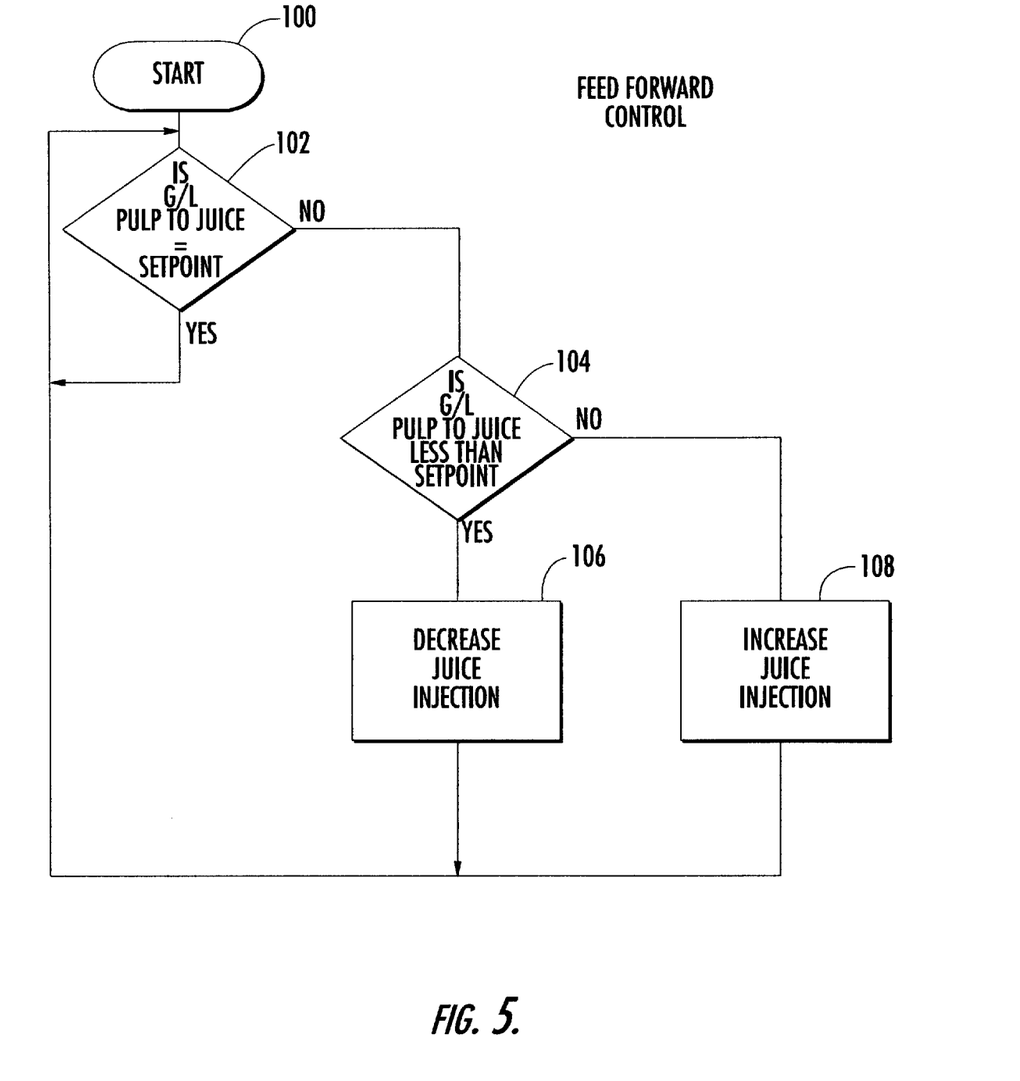
FIG. 5 is a flow chart illustrating a pulp concentration control system that could be used with a juice finisher, i.e., a juice (pulp) concentrator.

As shown in FIG. 5, at the start of the process (block 100), the gram/liter ratio of pulp-to-juice is determined and if it is at the setpoint (block 102), the loop continues. If it is not at setpoint, a determination is made whether the grams/liter of pulp-to-juice is less than setpoint (block 104). If yes, the juice injection is decreased (block 106) and if it is not less than setpoint, then the juice injection is increased (block 108).

It is evident that the present invention now allows greater control over pulp concentration during finishing and a measurement of pulp dryness for greater operating control over a juice finishing operation. An NMR sensor is much quicker than the prior art techniques and is repeatable.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A method of measuring pulp dryness comprising the steps of:
    obtaining a sample of pulp from a juice; and
    measuring the pulp dryness using a nuclear magnetic resonance (NMR) sensor.

2. The method according to claim 1, and further comprising the step of adjusting a juice and pulp processing system for separating pulp from juice in a predetermined amount based on the measured pulp dryness.

3. The method according to claim 2, and further comprising the step of comparing the measured pulp dryness with a predetermined setpoint, and adjusting the juice and pulp processing system to change the pulp dryness of pulp produced from the system.

4. A method of controlling the discharge of pulp and juice from a juice finisher, comprising the steps of:

measuring discharge from a juice finisher that processes pulp and juice using a nuclear magnetic resonance (NMR) sensor; and based on the results of the NMR measurement, regulating one of at least
 a) the juice injection into the juice finisher;
 b) the speed of the juice finisher; or
 c) discharge pressure from the juice finisher.

5. The method according to claim 4, and further comprising the step of measuring with the NMR sensor the pulp dryness discharged from the juice finisher, and comparing the pulp dryness with a predetermined setpoint, and if the pulp dryness differs from the predetermined setpoint, changing the speed of the juice finisher.

6. The method according to claim 5, wherein if the measured dryness is less than the predetermined setpoint, decreasing the speed of the finisher, and if the measured dryness is greater than the predetermined setpoint, increasing the speed of the finisher.

7. The method according to claim 6, wherein the juice finisher comprises a paddle type finisher.

8. The method according to claim 4, and further comprising the step of measuring with the NMR sensor the pulp dryness of pulp discharged from the juice finisher and comparing the pulp dryness with a predetermined setpoint, and if the pulp dryness differs from the predetermined setpoint, changing the pressure within the juice finisher.

9. The method according to claim 8, wherein if the measured dryness is less than the predetermined setpoint, decreasing pressure, and if the measured dryness is greater than the predetermined setpoint, increasing pressure.

10. The method according to claim 4, and further comprising the step of measuring with the NMR sensor the ratio of pulp to juice after the juice finisher and comparing the measured results with a predetermined setpoint, and if the measured results differ from the setpoint, changing the juice injection into the finished pulp for maintaining a desired pulp concentration level.

11. The method according to claim 10, wherein if the measured results are less than the setpoint, decreasing juice injection into the finished pulp, and if the measured results are above the setpoint, increasing the juice injection into the finished pulp.

12. The method according to claim 10, wherein the juice finisher comprises a screw type juice finisher.

13. The method according to claim 12, and further comprising the step of measuring the juice discharged from the juice finisher to aid in verifying the ratio of pulp to juice.

14. A method of controlling the concentration of pulp from a juice finisher comprising the steps of:

extracting a juice and pulp mixture from a fruit extractor;

feeding the juice and pulp mixture into a juice finisher to separate juice from a juice and pulp mixture;

determining the pulp concentration by measuring with a nuclear magnetic resonance (NMR) sensor the ratio of pulp to juice and comparing the measured results with a predetermined setpoint, and if the measured results are less than the setpoint, decreasing juice injection into the finished pulp, and if the measured results are greater than the setpoint, increasing juice injection into the finished pulp; and mixing juice recovered from the juice finisher into a mixer with the juice and pulp mixture to provide a desired mix.

15. The method according to claim 14, and further comprising the steps of:
 a) capturing juice from the juice finisher within a juice tank;
 b) pumping juice from the juice tank into the mixer;
 c) measuring the flow of juice pumped from the tank into the mixer; and
 d) changing the flow of juice from the juice tank based on the pulp concentration determined by the NMR sensor.

16. The method according to claim 14, and further comprising the step of pasteurizing the mixed juice and pulp after mixing.

17. A system for controlling the discharge of pulp and juice from a juice finisher comprising:

a juice finisher that receives juice and pulp from a juice extractor and separates the juice and pulp into a discharge substantially of pulp and a discharge substantially of juice;

a nuclear magnetic resonance (NMR) sensor for measuring the dryness of the pulp discharged from the juice finisher; and a controller for comparing the measured dryness with a predetermined setpoint and outputting a finisher control signal to the juice finisher for changing operation of the finisher.

18. The system according to claim 17, and further comprising a variable speed drive operatively connected to said juice finisher and responsive to said finisher control signal for decreasing the speed of the juice finisher if the measured dryness is less than a predetermined setpoint, and increasing the speed of the juice finisher if the measured dryness is greater than a predetermined setpoint.

19. The system according to claim 17, and further comprising a current-to-pressure transmitter connected to said juice finisher and responsive to said finisher control signal for decreasing pressure of the juice finisher when the measured dryness is less than the predetermined setpoint and increasing pressure of the juice finisher when the measured dryness is greater than the predetermined setpoint.

20. The system according to claim 17, wherein said controller determines the ratio of pulp to juice in the juice and pulp mixture.

21. The system according to claim 20, and further comprising a mixer for receiving a juice and pulp mixture and a portion of juice fed back from the juice finisher, and a valve operatively connected to said controller and operative for changing the flow of juice into the mixer.

* * * * *